United States Patent
Reed

(12) United States Patent     (10) Patent No.: US 6,689,137 B2
Reed     (45) Date of Patent: Feb. 10, 2004

(54) ORTHOPEDIC FASTENER AND METHOD

(76) Inventor: Gary Jack Reed, 1015 S. Soderquist Rd., Turlock, CA (US) 95380

( * ) Notice: Subject to any disclaimer, the term of this patent is extended or adjusted under 35 U.S.C. 154(b) by 0 days.

(21) Appl. No.: 09/978,490

(22) Filed: Oct. 15, 2001

(65) Prior Publication Data

US 2003/0074004 A1 Apr. 17, 2003

(51) Int. Cl.$^7$ ............................................. A61B 17/56
(52) U.S. Cl. ........................................... 606/73; 606/65
(58) Field of Search ........................... 606/73, 104, 62, 606/65, 72; 411/178, 411, 424, 354

(56) References Cited

U.S. PATENT DOCUMENTS

| | | | | |
|---|---|---|---|---|
| 4,175,555 A | * | 11/1979 | Herbert | 606/73 |
| 4,177,524 A | * | 12/1979 | Grell et al. | 606/86 |
| 5,019,079 A | * | 5/1991 | Ross | 606/72 |
| 5,499,892 A | * | 3/1996 | Reed | 411/5 |
| 5,536,127 A | * | 7/1996 | Pennig | 411/413 |
| 5,800,107 A | * | 9/1998 | Giannuzzi et al. | 411/386 |
| 6,048,344 A | * | 4/2000 | Schenk | 606/73 |
| 6,053,916 A | * | 4/2000 | Moore | 606/61 |
| 6,435,788 B2 | * | 8/2002 | Reed | 411/178 |
| 6,454,768 B1 | * | 9/2002 | Jackson | 606/61 |
| 6,572,315 B1 | * | 6/2003 | Reed | 411/307 |

* cited by examiner

*Primary Examiner*—Pedro Philogene
*Assistant Examiner*—David A Bonderer
(74) *Attorney, Agent, or Firm*—Bernhard Kreten

(57) ABSTRACT

An orthopedic fastener having compressive forces along the direction of the long axis of the fastener and radially inwardly directed forces towards the center of the fastener to draw in a bone providing an improved structure for uniting a fractured bone.

4 Claims, 2 Drawing Sheets

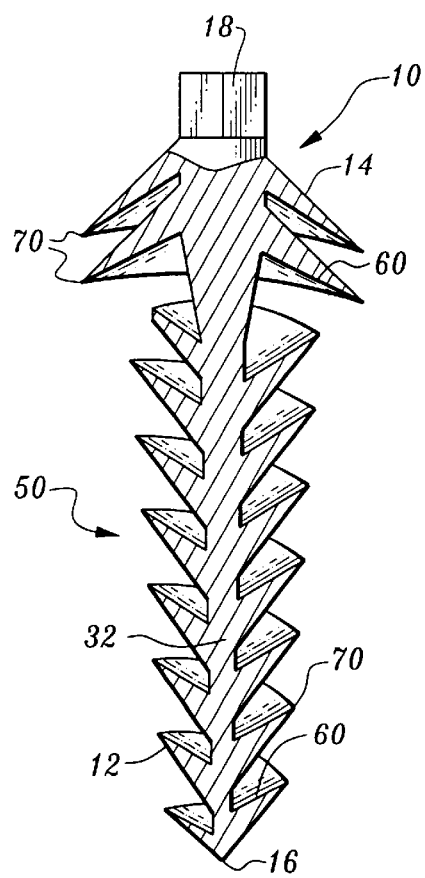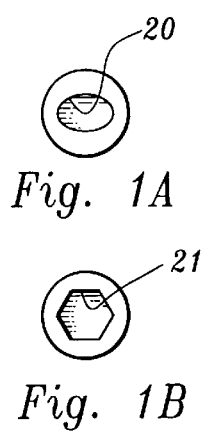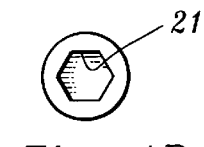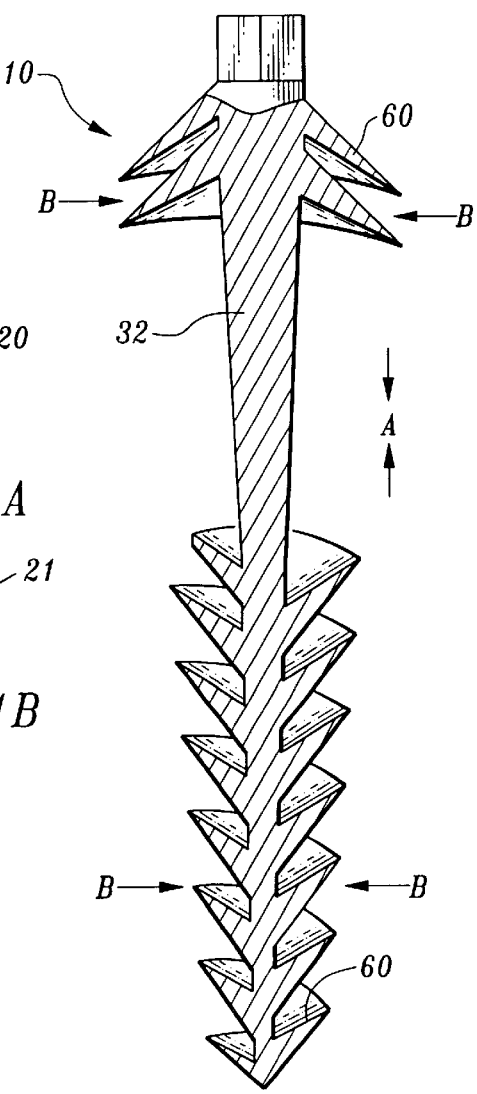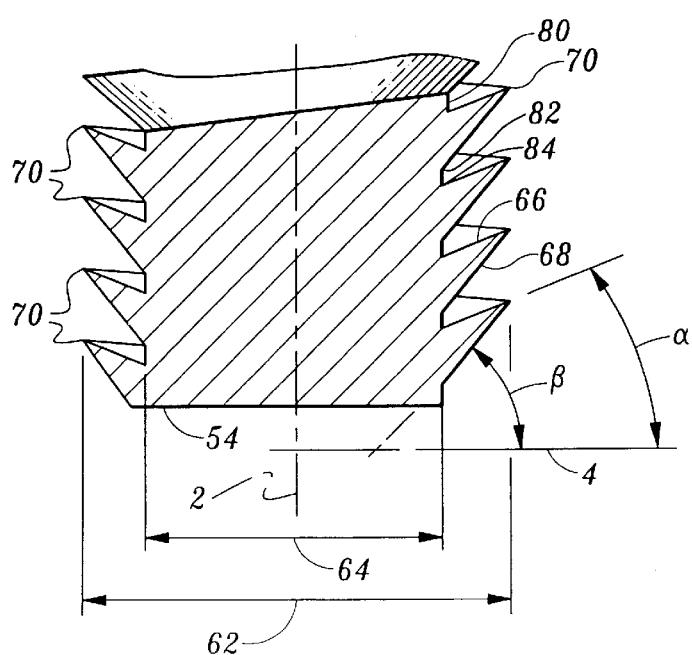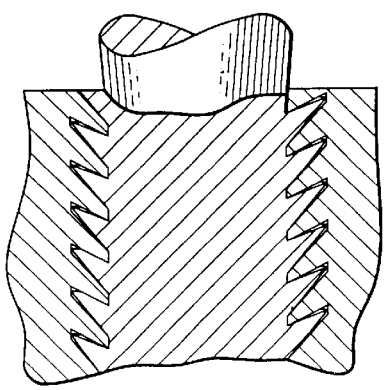
Fig. 1
Fig. 1A
Fig. 1B
Fig. 2
Fig. 3
Fig. 4

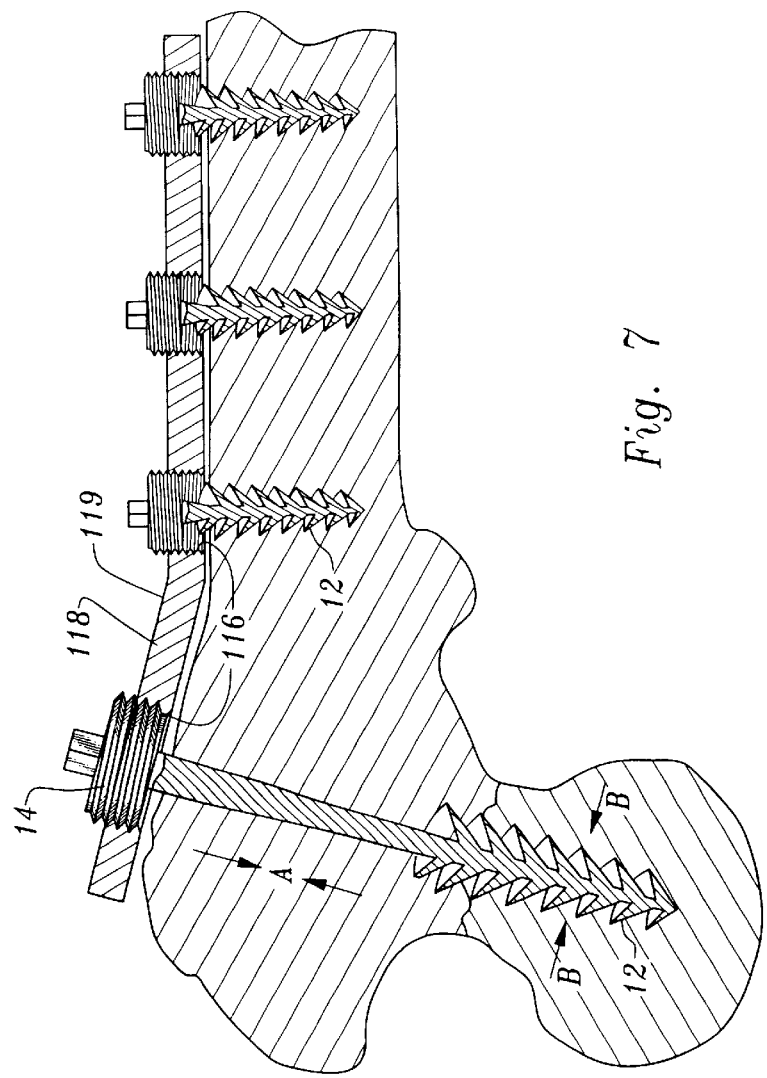
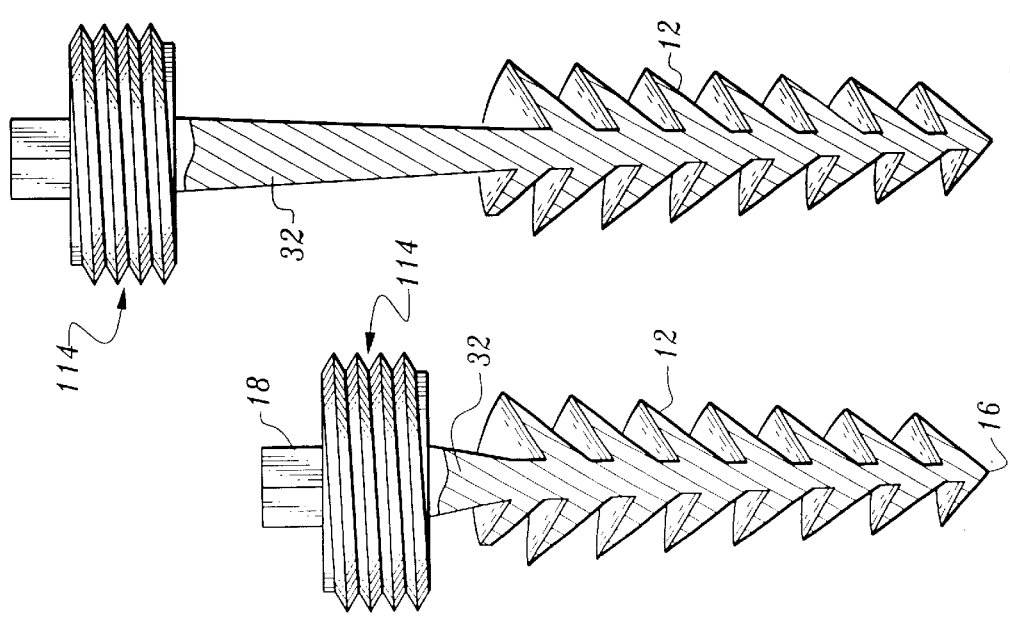

ORTHOPEDIC FASTENER AND METHOD

FIELD OF THE INVENTION

The following invention related generally to fasteners used by orthopedic surgeons in surgery. Specifically, the fastener according to the instant invention provides both axial (compressive) loading along the length of the fastener as well as radially inwardly forces (relative to the fastener shaft) on the bone to which the fastener is applied.

BACKGROUND OF THE INVENTION

Orthopedic surgeons typically are required to repair fractures and use pins in support thereof. The conventional pin actually induces a radially outwardly directed spreading force which does little to assist (and actually retards) the bone to mend itself. Further these pins induce no axial, compressive forces.

SUMMARY OF THE INVENTION

The instant invention is distinguished over the known prior art in that a fastener is disclosed which provides radially inwardly directed forces relative to the fastener shaft which draw in the bone with respect to the fastener to provide a preferred fastening structure. In addition, the instant invention induces compressive forces along the length of the fastener to facilitate a tight juncture at the area of the fracture to promulgate healing and resist flexing at the fracture.

OBJECTS OF THE INVENTION

The object of the present invention is to provide an improved orthopedic fastener exhibiting axial compressive forces and radially inward directed forces.

Viewed from a first vantage point, it is an object of the present invention to provide an orthopedic fastener having first and second thread portions disposed along a long axis of the fastener in which the first and second thread patterns induce radially inward drawing forces as well as axially compressive forces with respect to the direction of the long axis of the fastener.

BRIEF DESCRIPTION OF THE DRAWINGS

FIG. 1 is a view of one fastener.

FIG. 1A is a top view of another fastener drive.

FIG. 1B is a top view of a third fastener drive.

FIG. 2 is a view of a longer fastener, having an unthreaded medial shaft portion.

FIG. 3 is a sectional view of a variation of the fastener geometry along a small length in which the shaft is not tapered.

FIG. 4 is a sectional view similar to FIG. 3 but includes the tapered shaft.

FIG. 5 is an alternative to FIG. 1.

FIG. 6 is an alternative to FIG. 2.

FIG. 7 shows the FIGS. 5 and 6 fasteners deployed as one example.

DESCRIPTION OF PREFERRED EMBODIMENTS

Referring to the drawings, wherein like numerals denote like parts, reference numeral 10 is directed to the orthopedic fastener according to the present invention.

In its essence, the fastener 10 includes a threaded shaft 32 having a first thread pattern 12 at one end and a second thread pattern 14 at an opposite end. As shown in FIGS. 1 and 2, the first end thread pattern 12 terminates in a point 16 and the threads increase in diameter to form a thread pattern with its spiral increasing as it extends away from the point 16. A remote end 18, proximate the second thread pattern 14 includes a driving head 18 which in the drawings is shown as hexagonal, but can be formed as an alien wrench recess 21 (FIG. 1B), an oval drive head 20 (FIG. 1A), which is also recessed or other configuration to reliably drive the fastener. The second thread pattern 14 adjacent the drive head 18 preferably has a larger diameter but a similar thread contour which shall be discussed in detail infra. Preferably, the shaft 32 is of variable length and tapers and narrows from end 18 to point 16. Please see FIGS. 1 and 2.

A further nuance of the first and second thread patterns is that the first thread pattern 12 has a coarser thread than the second thread pattern 14 which is a finer thread. The point 16 is the point of initiation for insertion into a bone during an orthopedic procedure at a fracture site. To facilitate same, a pilot hole may be drilled in the bone but thereafter, because of the tapering nature of the first thread 12, this portion is thereafter self-threading. Notice that the crest 70 for both first and second thread patterns are sharp. This allows cutting into the bone which typically has a harder exterior than the interior. By providing a coarser thread pattern for the first thread 12, this thread will insert into the bone faster than the second thread pattern 14. As a consequence, when the bone begins to be engaged by the second thread pattern, an axial compression of the bone occurs along the direction of the two arrows A. In addition, because of the thread geometry, the threads will exert a radially inwardly directed force along the direction of the double-ended arrows B. Whereas in the prior art, conventional fasteners induced radially outwardly spreading (the opposite direction from arrow B), the instant invention provides radially inwardly or a drawing force as well as the compressive force A.

Notice in FIG. 3 that the shaft 32 is not tapered, but of constant cross section along its length. The threads 60 for each the first and second threads 12 and 14 are actually continuous helically wound thread which begins at the ends and spirals towards the medial portion of the shaft 32 as it migrates from the end. Notice also flat wall 54 may replace point 16 for any of the embodiments. With flat wall 54 the pilot hole is cut deeper and perhaps wider.

The threads 60 include a sharpened crest 70 defining a major diameter 62 of the threads and a root 80 defining a minor diameter 64 of the threads 60. As shown in detail in FIG. 3, the threads 60 have an upper surface 66 which extends from a bottom edge 84 of the root 80 to the sharpened crest 70. The threads 60 also include a lower surface 68 which extends from a top edge 82 of the root 80 to the sharpened crest 70. Both the upper surface 66 and lower surface 68 angle toward the medial portion of the fastener as the surfaces 66, 68 extend from the root 80 to the crest 70.

In section, the surfaces 66, 68 extend linearly from the root 80 to the sharpened crest 70. However, as this contour is rotated helically about the threaded shaft 32 along with the threads 60, the upper surface 66 and lower surface 68 take on a curved surface appearance. This appearance is similar to that which would be formed by a linear section of the surface of a cone with a tip of the cone oriented downward and the cone rotated and translated upward along a central axis thereof. The upper surface 66 and lower surface 68 thus have a curved surface in three dimensions similar to that of a cone, but a linear character when viewed in section.

The upper surface 66 extends from the root 80 to the sharpened crest 70 at an upper surface angle α diverging from a reference plane orthogonal to the central long axis 2 of the fastener. The upper surface angle α is preferably 20° but could be any angle between 0° and 90°. The lower surface 68 extends from the root 80 to the sharpened crest 70 at a lower surface angle β with respect to the reference plane. The lower surface angle β is preferably 40° but could vary between 0° and 90°.

The upper surface angle α is preferably less than the lower surface angle β. In this way, the threads 60 are provided with greater thickness, and hence greater strength adjacent the minor diameter 64 than at the major diameter 62 and are thus more capable of bearing the loads experienced within the bone.

It is the angulation of the surfaces, especially upper surface 66 which encourages the radially inward drawing force. When the upper and lower thread patterns are considered, axial compressive force can be seen.

The second thread portion 14 has the same FIG. 3 geometry except that the threads are inverted, and as mentioned earlier are a finer thread (greater threads per inch axially) than the first thread portion 12. In other words FIG. 3 would be viewed upside down for threads 14.

As mentioned in FIG. 3, the shaft 32 is not tapered, but of constant cross section, preferably along its length. Also FIG. 3 shows an end 54 which is flat and would benefit from predrilling a hole. FIG. 4 shows a similar thread detail, however the shaft 32 is tapered as per FIGS. 1 and 2. This depiction tracks the threads 12 of FIGS. 1 and 2. The threads 14 are similar but the taper of FIG. 4 is reversed.

FIGS. 5 through 7 show a variation where the tapered shaft 32 uses the specialized threads 12 of the FIG. 1 embodiment but conventional threads 114 on the second thread portion. The drive head 18 can be that of FIGS. 1, 1A, 1B or otherwise.

The conventional threads 114 mate with threaded bores 116 on a member 118 which may have a contour which follows the anatomy of the bone to be supported. Thus member 118 may have a compound contour as exemplified by the angulation 119. As shown, the thread 12 is embedded in the patient's bone. In the embodiment, the threads 12 coact with the threads 114 to provide the axial compression A and the threads 12 also provide the radically inward force B described in the earlier figures.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An orthopedic fastener, comprising in combination:

a bone engaging shaft having a first thread pattern at one end and a second thread pattern at another end, one said thread pattern being bone engaging and having means to draw radially inward bone within which it is embedded.

2. The fastener of claim 1 wherein said thread patterns include a sharpened crest having a major diameter and a root defining a minor diameter, said threads having an upper surface extending from a bottom edge of said root to said sharpened crest and a lower surface extending from a top edge of said root to said sharpened crest, said surfaces angle to a medial portion of said fastener.

3. The fastener of claim 2 wherein said upper surface defines a lower angle of inclination than said lower surface.

4. A method for deploying an orthopedic fastener into a bone, the steps including inserting the fastener into the bone to induce axial compressive forces and radially inwardly directed forces with respect to the fastener.

* * * * *